United States Patent [19]

Moser

[11] Patent Number: Plant 7,369

[45] Date of Patent: Oct. 30, 1990

[54] HIBISCUS PLANT NAMED ALOHA PINK

[75] Inventor: Frank C. Moser, Alva, Fla.

[73] Assignee: Yoder Brothers, Inc., Barberton, Ohio

[21] Appl. No.: 396,975

[22] Filed: Aug. 22, 1989

[51] Int. Cl.[5] ..... A01H 5/00

[52] U.S. Cl. ..... Plt./54

[58] Field of Search ..... Plt./54

*Primary Examiner*—Howard J. Locker

*Attorney, Agent, or Firm*—Foley & Lardner, Schwartz, Jeffery, Schwaab, Mack, Blumenthal & Evans

[57] ABSTRACT

A Hibiscus plant named Aloha Pink particularly characterized by its light pink flower color, with a darker pink throat followed by a dark red eye; regular flower form, flower 9 cm. in diameter, excellent pot habit, vigorous growth, excellent branching; dark red eye is not solid, the right one-third of each petal base being white creating the effect of a white star amid the dark red eye; flower life a single day, easy to propagate, excellent resistance to bacterial leaf spot (Pseudomonas sp.), and good shipping tolerance (Bud Drop Resistance).

2 Drawing Sheets

The present invention comprises a new and distinct cultivar of Hibiscus, botanically known as *Hibiscus Rosa-sinensis* L., and referred to by the cultivar name Aloha Pink.

Aloha Pink, identified as 84-024-001 during the breeding and selection process, originated from a planned cross hybridization between two selected breeding lines in a controlled breeding program in Fort Myers, Fla. by Frank C. Moser.

The female, or seed parent is a breeding line designated as code #0005 and the pollen, or male parent is a breeding line designated as code #0001.

Aloha Pink was discovered and selected as a flowering plant within the progeny of the stated cross by Frank C. Moser in July of 1984, outside in ground beds in Fort Myers, Fla.

The first asexual reproduction of Aloha Pink was accomplished when vegetative cuttings were taken from the initial plant selection in October of 1984 in Fort Myers, Fla. from plants grown outside in ground beds, by technicians working under formulations established and supervised by Frank C. Moser.

Horticultural examinations of controlled flowerings of successive generations of plants derived from cuttings taken from the original selection have shown that the unique combination of characteristics as herein disclosed for Aloha Pink are fixed and retained through successive generations of asexual reproduction.

Aloha Pink has not been observed under all possible environmental conditions. The phenotype may vary significantly with variations in environment such as temperature and light intensity.

The following observations, measurements and comparisons describe plants that were grown in Fort Myers, Fla. in a controlled greenhouse environment and following a commercial schedule.

The following traits have been repeatedly observed and are determined to be basic characteristics of Aloha Pink, which, in combination, distinguish this Hibiscus as a new and distinct cultivar:

1. Light pink flower color, with a darker pink throat followed by a dark red eye.

2. Regular flower form, flower about 9 cm. in diameter.

3. Excellent pot habit, vigorous growth, excellent branching.

4. Dark red eye is not solid, the right one third of each petal is white, creating the effect of a white star around the dark red eye.

5. Flower life of a single day.

6. Easy to propagate.

7. Excellent resistance to Bacterial Leaf Spot (Pseudomonas sp.).

8. Good shipping tolerance (Bud Drop Resistance).

The accompanying photographic drawings show typical habit, flower and leaf characteristics of Aloha Pink, with colors being as nearly true as possible with illustrations of this type. Sheet 1 is a color photograph of Aloha Pink grown as a commercially finished pot plant. Sheet 2 is a black and white photograph showing the variation in leaf shape that can characteristically be found on any one plant of Aloha Pink.

Of the commercial cultivars known to the inventor, the most similar in comparison to Aloha Pink is the cultivar Pink Versicolor.

Aloha Pink is similar to Pink Versicolor in that both cultivars produce pink flowers with red eyes. Both propagate easily, have attractive foliage and have excellent pot habit.

Aloha Pink differs from Pink Versicolor in that the flowers of Aloha Pink are smaller and a lighter shade of Pink. The eye of Aloha Pink differs from Pink Versicolor in that the base of each petal is one-third white and two-thirds dark red, producing a white star around the dark red eye, while the eye of Pink Versicolor is solid red. Aloha Pink is more upright in growth, has larger leaves and makes a fuller pot than Pink Versicolor. Aloha Pink is very resistant to Bacterial Leaf Spot, while Pink Versicolor is very susceptible. Aloha Pink has much better shipping tolerance (Bud Drop Resistance) than Pink Versicolor.

In the following description, color references are made to The Royal Horticultural Society Colour Chart. The color readings were taken from greenhouse grown plants on Jan. 16, 1989. All readings were taken in an office under cool white fluorescent lights, facing a west window between the hours of 10:00 A.M. and 2:00 P.M.

Classification:

*Botanical.*—*Hibiscus Rosa-sinensis* L. cv. Aloha Pink.

*Commercial.*—Greenhouse pot crop.

INFLORESCENCE

A. Flower (general):

*Size.*—9 cm.

*Borne.*—In axils of leaves, 1 per node.

*Form.*—Regular single.

*Life.*—1 day.

*Fragrance.*—None.

*Blooming habit.*—Continuously, year round.

B. Corolla (petals):

*Texture.*—Smooth, veins slightly raised.

*Substance.*—Medium thick.

*Shape.*—Rounded.

*Color.*—Eye: Red 46A alternating with white. Throat: Pink 52A (appears much darker in photograph due to light reflection). Zone: None. Body of petal: Veins — Pink 55A. Interveinal — Pink 55B. Edge: None.

C. Bud (one day prior to opening):

*Size.*—5 cm.

*Shape.*—Conical.

*Color.*—Base of bud — white. Body veins — Yellow 11B. Interveinal — Pink 52B. Tip of bud — Pink 52B.

Calyx: Cup shaped, 5 pointed lobes, a single prominent midvein per lobe, membranous.

*Length.*—2.5 cm.

*Color.*—Green 144B.

E. Epicalyx: 6–8 pointed, narrow, sword-shaped bracts.

*Length.*—2.5–3.0 cm.

*Color.*—Green 137B.

F. Peduncle:

*Length.*—6.0–6.5 cm.

*Strength.*—Strong.

*Aspect.*—Smooth.

*Color.*—Green 144A.

G. Reproductive Organs:

1. *Androecium* (*stamens*).—Anthers: Numerous. Filments: 0.5 cm., Pink 47C. Pollen: Moderate. Color: Yellow 13A. Staminal column: Upper 30% antheriferous. Length: 6.5 cm. Color: Upper 70% — Pink 47C. Lower 30% — Red 46A.
2. *Gynoecium* (*pistil*).—Stigma: 5 in number, round, discoid, hairy. Color: Red 42A. Style: Length: 7.0 cm. Color: Yellow 10D. Branches: 5 in number. Color: Upper surface — Red 43C. Lower surface — White. Ovary: Rounded. Color: Yellow 7D.

PLANT CHARACTERISTICS

A. Foliage:

*Arrangement.*—Alternate.

*Shape.*—Juvenile: Heterophyllus. Mature: Cordate, serrate. Color: Dark Green 139A.

*Petiole.*—Length: 2.5 cm. Aspect: Smooth. Color: Green 143A.

*Stipules.*—Two per node, shape acicular (needle shaped). Color: Green 137A.

B. Stem: Aspect smooth, becoming woody with age.

C. Plant habit: Excellent.

D. Breaking action: Excellent.

E. Rooting: Excellent.

F. Growth Regulator: Required due to vigorous growth.

G. Low light bud initiation: Average.

H. Shipping Tolerance: Good.

I claim:

1. A new and distinct cultivar of Hibiscus plant named Aloha Pink, as described and illustrated.

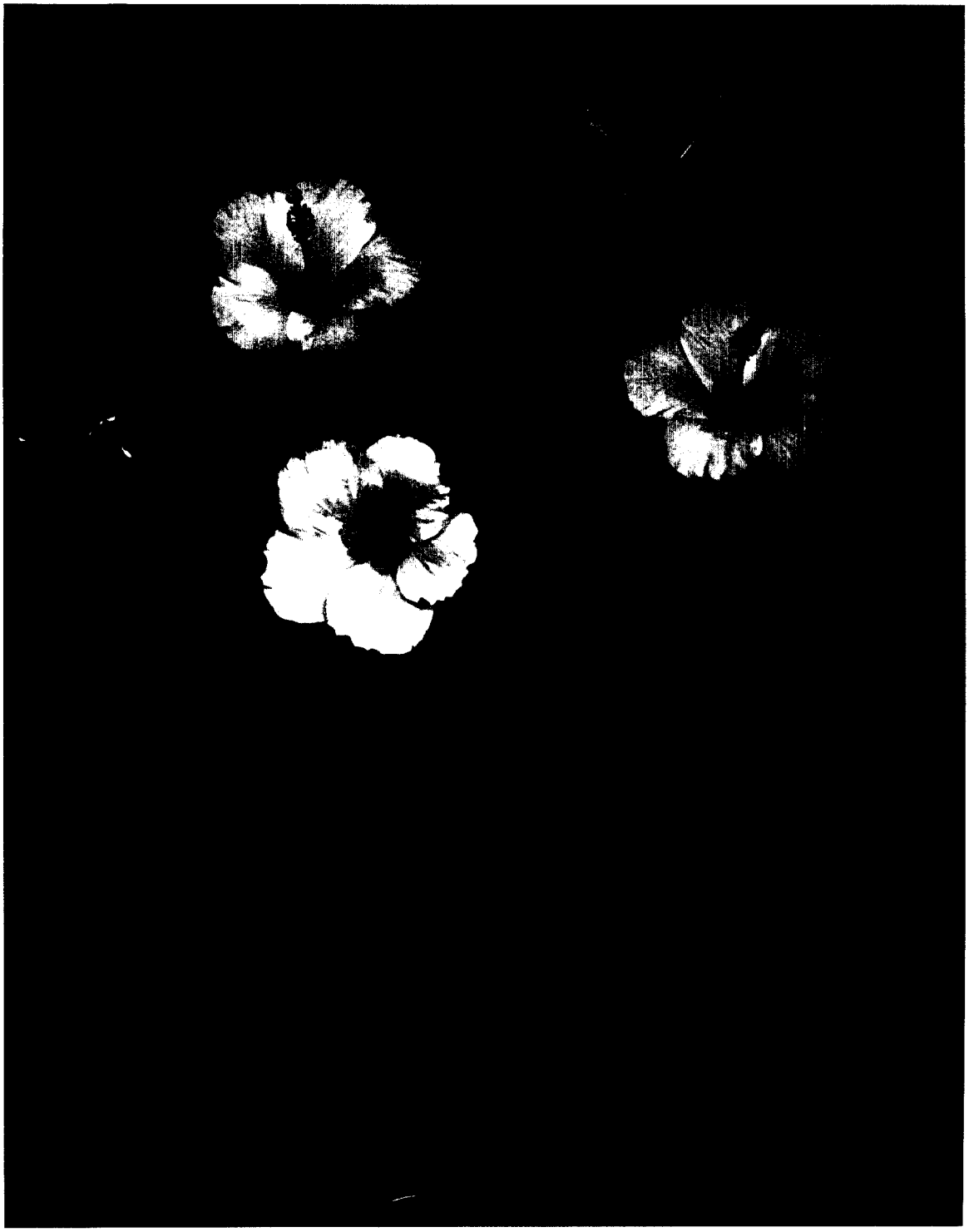

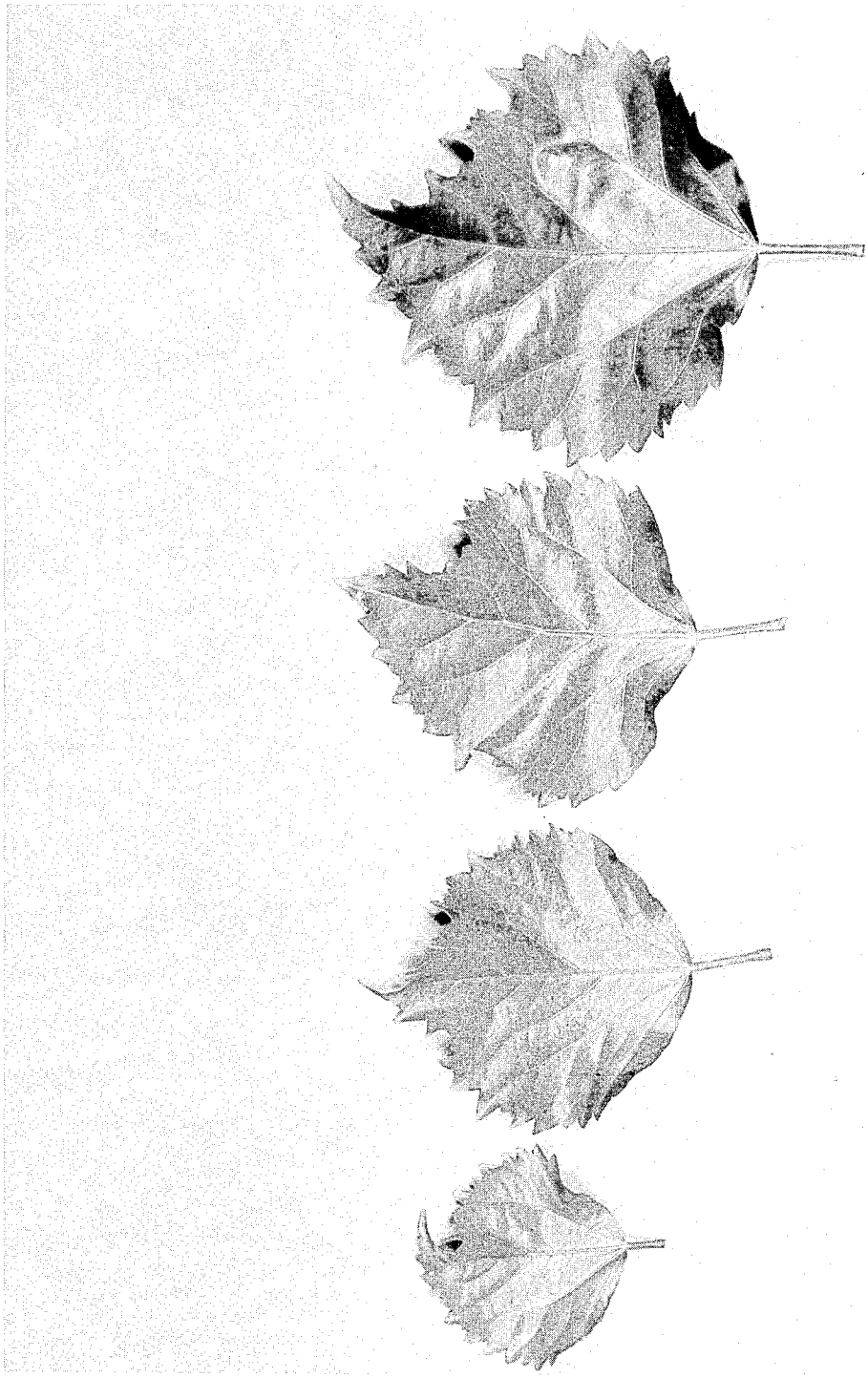

* * * * *